(12) United States Patent
Bertholds et al.

(10) Patent No.: US 10,299,826 B2
(45) Date of Patent: May 28, 2019

(54) NEEDLE FOR INVASIVE MEDICAL USE AND NEEDLE ASSEMBLY

(71) Applicant: Sensoptic SA, Losone (CH)

(72) Inventors: Axel Bertholds, Verscio (CH); Pere Llosas, Minusio (CH); Simon Henein, Neuchâtel (CH); Charles Baur, St. Aubin/Sauges (CH)

(73) Assignee: Sensoptic SA, Losone (CH)

(*) Notice: Subject to any disclaimer, the term of this patent is extended or adjusted under 35 U.S.C. 154(b) by 188 days.

(21) Appl. No.: 15/105,921

(22) PCT Filed: Dec. 16, 2014

(86) PCT No.: PCT/EP2014/078017
§ 371 (c)(1),
(2) Date: Jun. 17, 2016

(87) PCT Pub. No.: WO2015/091521
PCT Pub. Date: Jun. 25, 2015

(65) Prior Publication Data
US 2016/0310164 A1      Oct. 27, 2016

(30) Foreign Application Priority Data
Dec. 18, 2013    (CH) ...................................... 2094/13

(51) Int. Cl.
*A61B 17/34* (2006.01)
*A61M 5/32* (2006.01)
(Continued)

(52) U.S. Cl.
CPC ...... *A61B 17/3403* (2013.01); *A61B 17/3401* (2013.01); *A61B 17/3494* (2013.01);
(Continued)

(58) Field of Classification Search
CPC ................ A61B 17/3403; A61B 90/06; A61B 2090/065; A61B 2090/3614; A61B 2090/064; A61M 5/329
See application file for complete search history.

(56) References Cited

U.S. PATENT DOCUMENTS 6,612,992 B1 * 9/2003 Hossack .................. A61B 8/12
600/467
2006/0106315 A1    5/2006 Edens
(Continued)

FOREIGN PATENT DOCUMENTS

| EP | 1884211 | 2/2008 |
|---|---|---|
| EP | 2626680 | 8/2013 |

(Continued)

OTHER PUBLICATIONS

International Preliminary Report on Patentability dated Jun. 21, 2016 for PCT/EP2014/076017.
(Continued)

*Primary Examiner* — Bradley J Osinski
(74) *Attorney, Agent, or Firm* — Paul D. Bianco; Gary S. Winer; Fleit Gibbons Gutman Bongini & Bianco PL

(57) ABSTRACT

A needle for invasive medical use includes a long extended cylindrical needle shaft having an axis and an outer surface area, with a short shaft end at a first end of the shaft with a beveled tip with a pointed end, and a needle hub attached to a second end of the shaft including a device to indicate the location of the shaft end during use inside a body. The needle has a flexible joint with a notch within the shaft at the beginning of the shaft end. The device is a displacement sensor for detecting a displacement of the shaft end relative to the rest of the shaft resulted from a force applied to the shaft end when the needle hub is moved and a signal conductor to transmit the detected signals. The invention further describes a needle assembly comprising such a (Continued)

Figure 1:
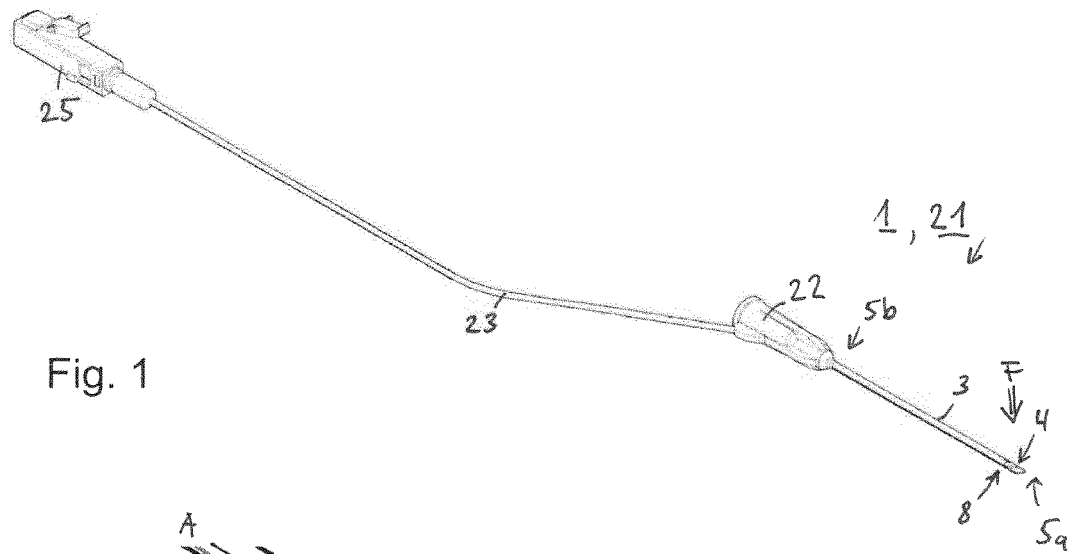

needle and a syringe attached to said needle hub, whereas an evaluation unit is connected to the signal conductor.

20 Claims, 3 Drawing Sheets

(51) Int. Cl.
*A61B 90/00* (2016.01)
*G01L 5/16* (2006.01)

(52) U.S. Cl.
CPC .......... *A61B 90/06* (2016.02); *A61B 90/361* (2016.02); *A61M 5/329* (2013.01); *A61M 5/3286* (2013.01); *A61B 2090/061* (2016.02); *A61B 2090/064* (2016.02); *A61B 2090/065* (2016.02); *A61B 2090/3614* (2016.02); *G01L 5/161* (2013.01); *G01L 5/166* (2013.01)

(56) References Cited

U.S. PATENT DOCUMENTS

| | | | |
|---|---|---|---|
| 2008/0097378 A1 | 4/2008 | Zuckerman | |
| 2008/0294144 A1* | 11/2008 | Leo | A61B 5/6885 604/508 |
| 2009/0069673 A1 | 3/2009 | Tapalian et al. | |
| 2009/0177095 A1* | 7/2009 | Aeby | A61B 5/0084 600/478 |
| 2010/0228194 A1 | 9/2010 | Freeman et al. | |
| 2011/0054353 A1* | 3/2011 | Hulvershorn | A61B 5/032 600/587 |
| 2013/0204142 A1 | 8/2013 | Bertholds et al. | |
| 2014/0121538 A1 | 5/2014 | Hendriks et al. | |
| 2016/0022373 A1 | 1/2016 | Valsamis et al. | |

FOREIGN PATENT DOCUMENTS

| | | |
|---|---|---|
| WO | 2006055529 | 5/2006 |
| WO | 2013001394 | 1/2013 |
| WO | 2013056243 | 4/2013 |
| WO | 2013150019 | 10/2013 |

OTHER PUBLICATIONS

International Search report completed Mar. 24, 2015 for PCT/EP2014/078017.
Written Opinion of the International Searching Authority published Jun. 25, 2015 for PCT/EP2014/078017.

* cited by examiner

NEEDLE FOR INVASIVE MEDICAL USE AND NEEDLE ASSEMBLY

TECHNICAL FIELD

The invention relates to a needle for invasive medical use comprising a long extended cylindrical needle shaft having an axis A and an outer surface area, with a short shaft end at a first end of the shaft with a beveled tip with a pointed end, and a needle hub attached to a second end of the shaft comprising a device to indicate the location of the shaft end during use inside a body. The invention also relates to a needle assembly comprising such a needle.

PRIOR ART

Medical needle interventions are a common technique for accessing tissue structures or organs that would be otherwise difficult to reach. In these procedures, needles are used, for example, to inject drugs, to insert catheters, to extract biopsy samples, to puncture vessels or to place radioactive seeds at tumor sites, to name a few.

As the effectiveness of the interventions is dependent on the accuracy of the needle positioning, practitioners must possess considerable skill and experience in order to control the needle path and the tip position with respect to the predetermined target. They rely upon force feedback from the handheld tool, correlated with their own mental three-dimensional visualization of anatomic structures.

Serious implications and undesired results may incur if the shaft end of the needle tip is unintentionally located outside the predetermined target. Additionally, practitioners must deal with anatomical differences of patients, disturbance of body motion, tissue deformation during needle insertion, cutting and friction forces as well as tip deflection during needle penetration.

In several needle interventions, practitioners must position accurately the tip in a liquid or gaseous space or cavity to be explored and treated. Examples are epidural injections in the epidural space, intra-articular injections in the synovial cavity and punctures inside veins.

To allow precise positioning of the needle in the predetermined target, today practitioners can take advantage of intra-operative medical imaging systems like ultrasound, X-ray fluoroscopy, computerized tomography and magnetic resonance imaging. All systems work well but are too expensive and complex in relation to the frequent and relatively simple intervention of inserting a needle with good precision.

As alternatives to imaging systems, to discriminate biological tissues during needle insertion, in US20100228194 A1 is described a needle guidance devices based on electrical impendence measurements. In WO2006055529 A2 an ultrasound technique is employed and in US2009069673 optical coherence tomography is used for exact needle positioning.

A particular case of application of the present invention relates to epidural injections to position needles accurately in the epidural space. The document WO2013/056243 A1 employs fiber optic inserts inside needles to detect different optical properties of tissues during penetration. Fiber optic inserts are also employed in the document EP1884211 A2 for needle navigation in joints and in WO2013/001394 A1 for inspection of cancerous tissues.

All listed methods and devices suffer from the inherent lack of space of standard needles or standard injection needles. Either they employ additional components to be inserted and removed from the needle lumen, or they affect considerably the shape and functionality of standard needles. In addition, most devices are relatively complex to operate, have difficulties in discriminating all tissues, are suited only for specific procedures or exhibit poor spatial resolution. The major drawback is that they are not compatible with standard commercial needles and with conventional injection procedures usually applied by practitioners.

DESCRIPTION OF THE PRESENT INVENTION

The problem of the known needles with means for assisting in needle navigation is that they are too complex in construction and often too large in diameter, resulting in too expensive devices. It would therefore be desirable to provide disposable needles or needle assemblies including simple means to assist practitioners to better and faster position needle tips in predetermined liquid or gaseous environments. These means should further not affect the dimensions and functionality of commercial needles. Further, such needles with such means must allow high volume cost effective production.

The problem can be solved by a needle according to the features described in the first patent claim. The invention describes an aforementioned needle, whereas the needle comprises a flexible joint with a notch within the shaft at the beginning of the shaft end.

Further, the needed device to indicate the location of the shaft end during use inside a body is a displacement sensor. It detects a displacement of the shaft end relative to the rest of the shaft resulted from a force F applied to the shaft end when the needle hub is moved. The displacement sensor comprises a signal conductor to transmit the detected signals to an evaluation device.

As long as the shaft end is surrounded by a liquid or a gas, no force is applied to it while moving the needle hub in small axial or lateral movements and no displacement of the shaft end relative to the rest of the shaft will be detected. But when the shaft end is surrounded by resistant tissue, any movement of the needle hub results in a force F applied to that shaft end, which again results in a displacement of the shaft end relative to the rest of the shaft due to the flexible joint at the beginning of the shaft end. This displacement is detected by the displacement sensor at the flexible joint. The displacement sensor receives this information and leads it by the signal conductor to an evaluation unit for further analysis.

The displacement sensor measures the varying width of the notch at the flexible joint, preferably by interferometry or by a strain gauge.

Such an inventive medical needle permits "in vivo" and "in situ" detection of contact forces exerted at the shaft end during injection procedures, for example. In particular, the invention provides a needle and a needle assembly which allows confirming correct placement of conventional needles and injection needles in predetermined liquid or gaseous spaces in biological materials.

According to a first embodiment of the invention, the displacement sensor is an optical sensor which comprises an optical fiber positioned inside the shaft with a fiber end positioned inside the notch facing a reflective surface attached to the shaft end. The optical fiber sends out light which is reflected at its fiber end as well as at the reflective surface at the shaft end, receives this reflected light and leads it as a signal conductor to an evaluation unit for further analysis. This requires only one single optical fiber in the shaft, which leads to an easy construction of the needle and results in a cheap production for the manufacturing of the needle.

According to an alternative embodiment of the invention, the displacement sensor comprises a miniature electric strain gauge at the flexible joint, connected with a pair of wires, whereas the signal conductor contains the wires. The strain gauge may be placed at the flexible joint, where it measures tension and compression, when the shaft end is moved relative to the rest of the shaft. But in a preferred embodiment, the strain gauge is mounted under tension in the notch, fixed at the shaft and at the shaft end bridging the notch.

As long as a variation of the width of the notch is detected while moving the needle hub, the shaft end is not surrounded by liquid or gas. This means for example that it is not safe at that time to inject a drug in a vessel. On the other hand, when no variation of the width of the notch is detected while moving the needle hub, the needle shaft end is surrounded by liquid or gas, a drug can be injected in this liquid or gas.

SHORT DESCRIPTION OF THE DRAWINGS

Figure 2:
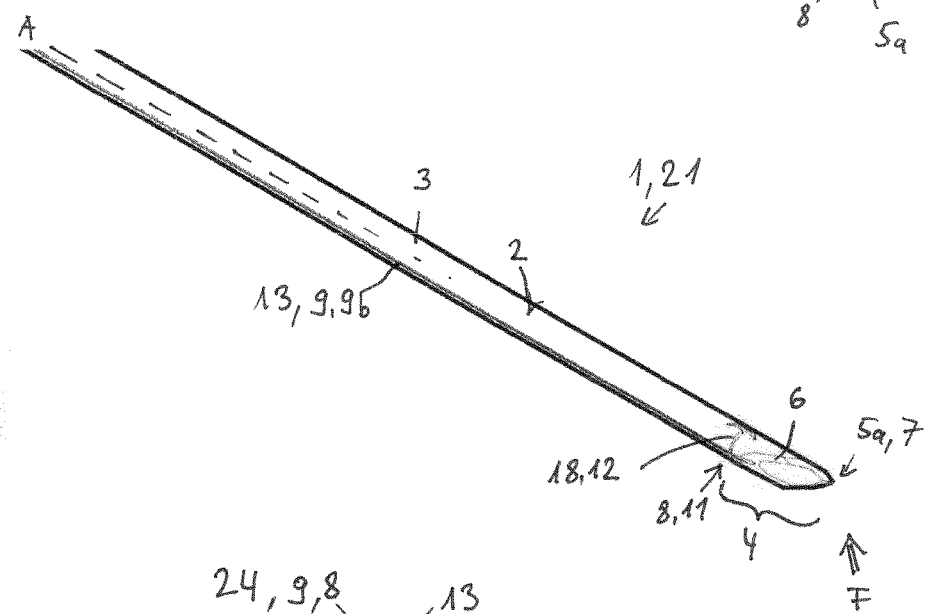
Figure 4:
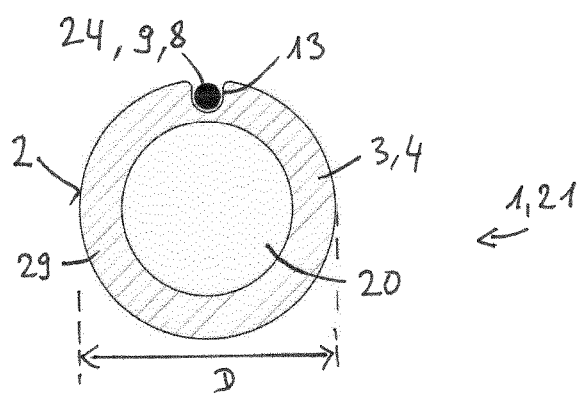
Figure 3A:
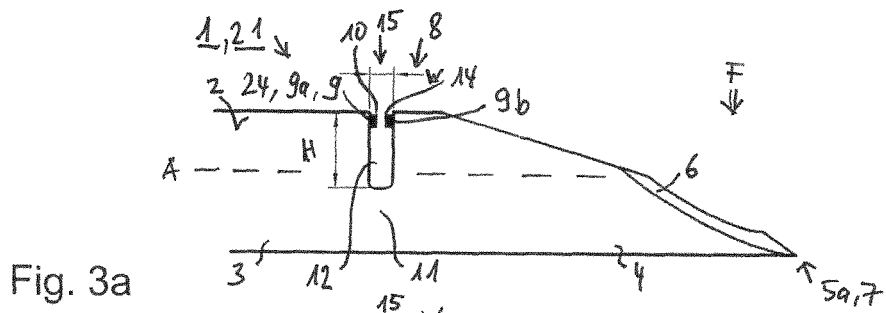
Figure 3B:
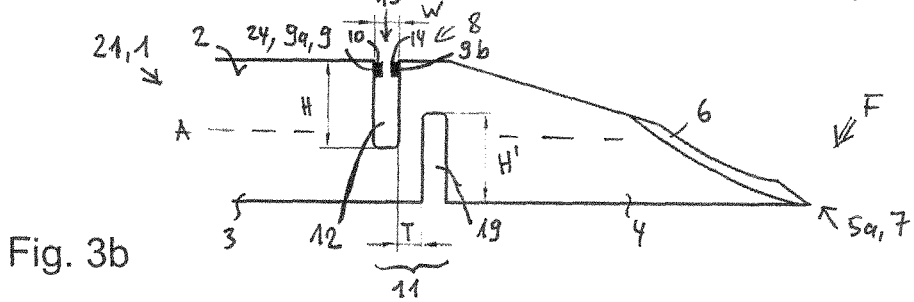
Figure 3C:
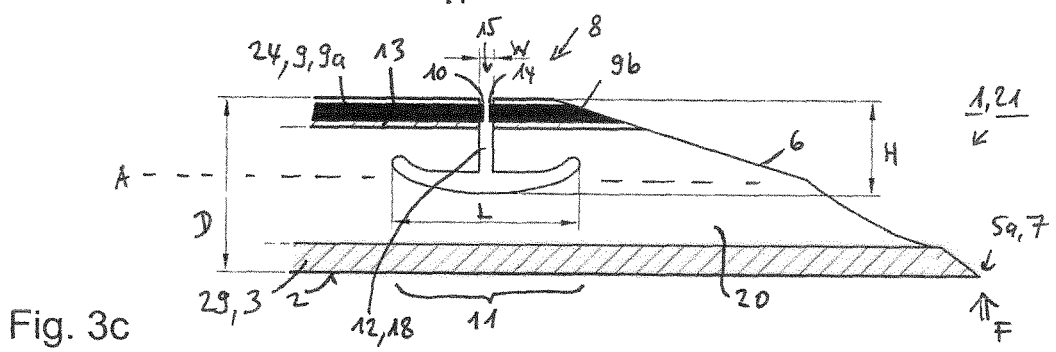
Figure 3D:
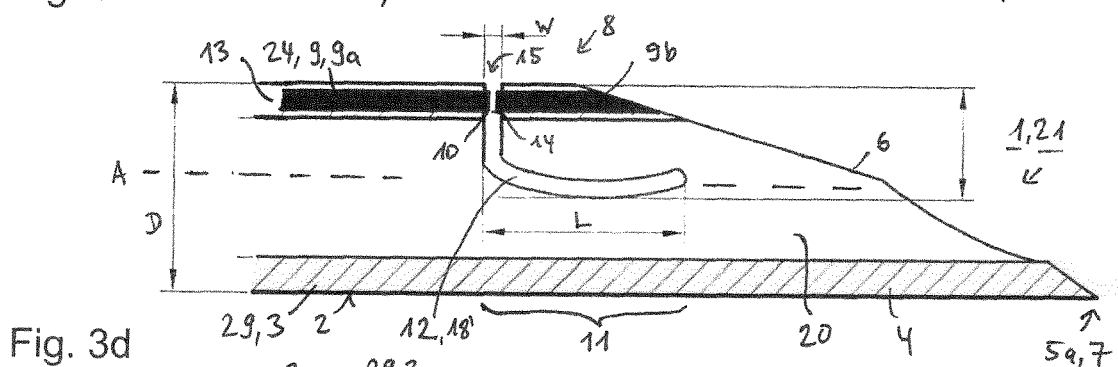
Figure 3E:
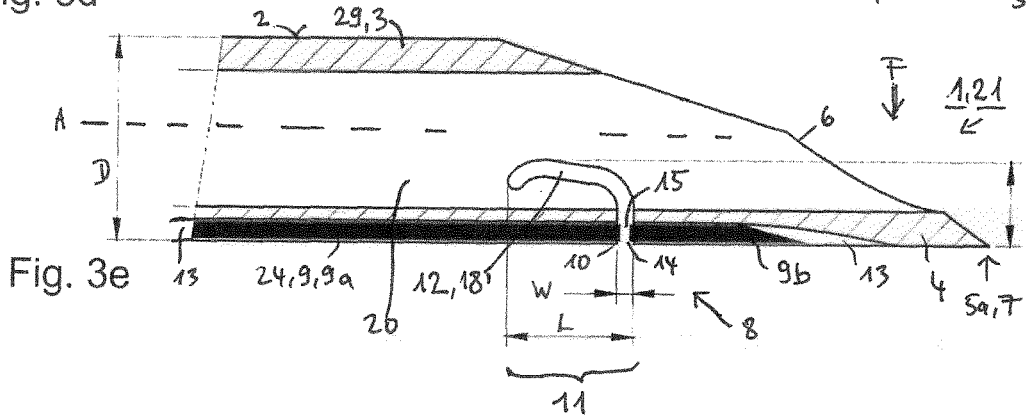
Figure 5:
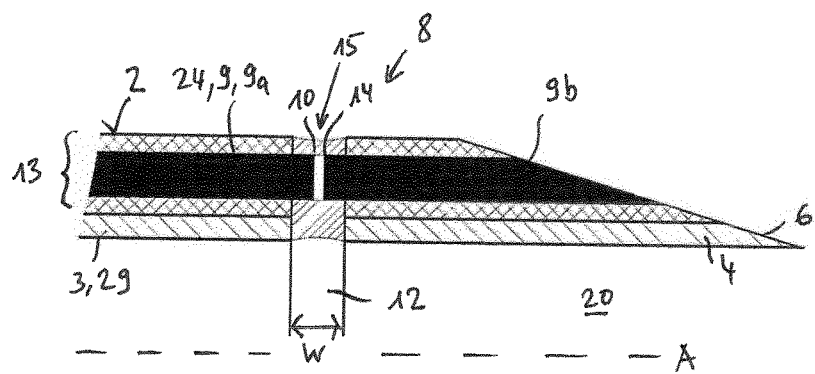
Figure 6:
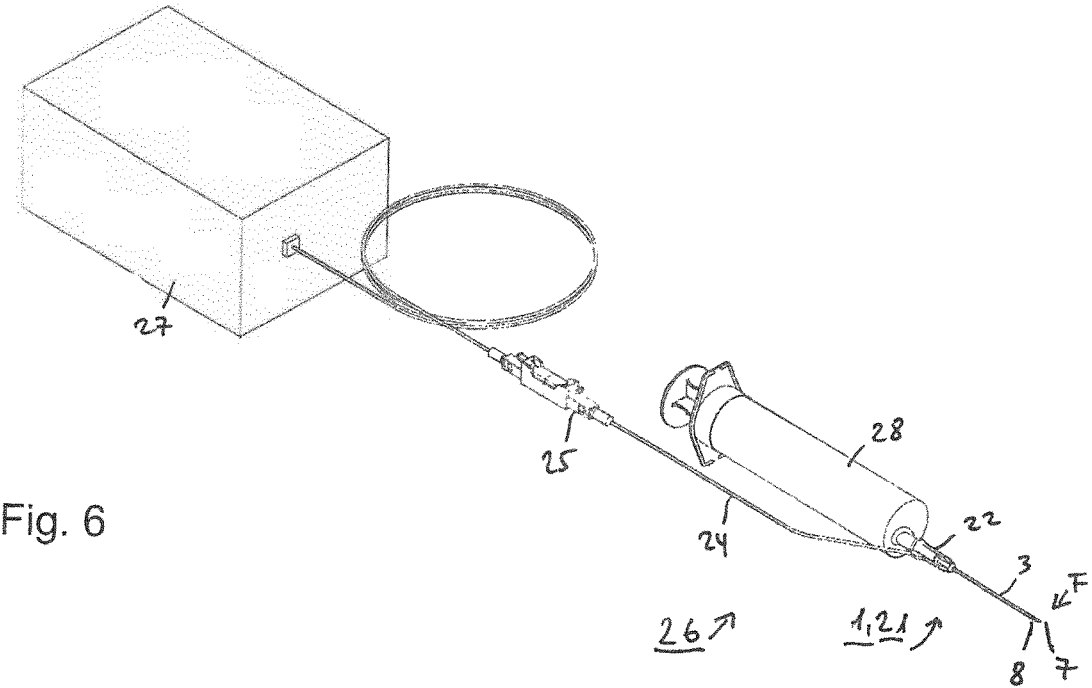

In the following the invention is illustrated in more detail with respect to the drawings. All same numerals in all drawings identify same objects. Shown are FIG. 1 an inventive needle in a preferred embodiment;

FIG. 2 a perspective view of a section of an inventive needle shaft;

FIG. 3a a side view of an inventive needle shaft at its first end;

FIG. 3b a side view of an inventive needle shaft at its first end in an alternative configuration;

FIG. 3c a longitudinal cross sectional view of an inventive needle shaft at its first end in another alternative configuration;

FIG. 3d a longitudinal cross sectional view of an inventive needle shaft at its first end in a further alternative configuration;

FIG. 3e a longitudinal cross sectional view of an inventive needle at the tip in a further alternative configuration;

FIG. 4 a cross sectional view of an inventive hollow needle shaft;

FIG. 5 a longitudinal cross sectional view of a section of a needle shaft in an inventive configuration at the displacement sensor;

FIG. 6 an inventive assembly ready for use.

WAYS OF CARRYING-OUT THE INVENTION

FIG. 1 shows an inventive needle 1 for invasive medical use comprising a long extended cylindrical needle shaft 3 with a short shaft end 4 at a first end of the shaft 5a and a needle hub 22 attached to a second end of the shaft 5b. The short shaft end 4 comprises a beveled tip 6 with a pointed end 7, better shown in FIG. 2. The needle 1 further comprises a device to indicate the location of the shaft end 4 during use inside a body. This information is led by a signal conductor 24, shown in FIGS. 3 and 4, passing the needle hub 22 and a cable 23 attached to said needle hub 22, to a connector 25.

FIG. 2 shows a zoomed view of the needle shaft 3 shown in FIG. 1. The FIGS. 3a-3e show further zoomed views of a shaft 3 near its shaft end 4 in various configurations.

The shaft 3 has an axis A and an outer surface area 2. The needle 1 further comprises the said device, which is a displacement sensor 8 for detecting a displacement of the shaft end 4 relative to the rest of the shaft 3 resulted from a force F applied to the shaft end 4. A flexible joint 11 with a notch 12 is arranged within the shaft 3 located at the beginning of the shaft end 4, allowing a relative movement from the shaft end 4 relative to the rest of the shaft 3. In this first inventive embodiment, the displacement sensor 8 comprises an optical fiber 9 with a first portion 9a positioned inside the shaft 3, with a fiber end 10 positioned inside the notch 12 facing a reflective surface 14 fixed to the shaft end 4 and forming a parallel gap 15 between the fiber end 10 and the reflective surface 14.

As shown in the FIG. 2, the displacement sensor 8 is integrated in the needle 1, in particular in the needle shaft 3. The first portion of the optical fiber 9a detects a force F applied to the shaft end 4 by measuring the varying distance between the fiber end 10 and the reflective surface 14 at the shaft end 4.

For a measurement, light is transmitted through the first portion of the optical fiber 9a and partially emitted from the fiber end 10 to an opposed reflective surface 14 at the shaft end 4 where it is reflected. A part of the reflected light is re-entering the first portion of the optical fiber 9a through its fiber end 10, transmitted through the first portion of the optical fiber 9a being a signal conductor and finally reaching a connector 25 and entering an evaluation unit 27, shown in FIG. 6. Alternatively, the first portion of the optical fiber 9a can lead directly to an evaluation unit 27 without passing a connector 25.

A part of the light is not emitted from the fiber end 10 but reflected back to the fiber 9 at the fiber end 10. In the evaluation unit, the light reflected at the fiber end 10 is compared to the light reflected at the reflective surface 14. By analyzing the reflected light, the evaluation unit 27 can first determine the distance between the fiber end 10 and the opposed reflective surface 14 and further determine a displacement of the shaft end 4, which is dependent to a force F applied to the shaft end 4. This measurement can be done by any known measurement method, e.g. using white light or monochromatic light, e.g. by interferometry or intensity measurements. If the difference between the two reflected light signals is within its normal range, no force is applied at the shaft end 4. But if the timely difference is too long or too short, a force is applied. In this case, a visual or acoustical signal may be given as an alarm, if desired.

Since there is a flexible joint 11 in the shaft 3 at the beginning of the shaft end 4, a displacement is detected by the displacement sensor 8 as soon as the hub 22 is moving the shaft 3 and the shaft end 4 is in touch with anything different than liquid or gas.

Preferably, the first notch 12 is transverse to the axis A, at least in the section with a fiber end 10 and the reflective surface 14, whereas the first fiber end 10 is positioned within this first notch 12. The first notch 12 is a cut deep through the shaft 3, preferably passing about or more than half of the shaft 3, leaving a portion to build out the flexible joint 11 at the beginning of the shaft end 4. The first notch 12 is wide enough to allow the shaft end 4 to move towards and away from the rest of the shaft 3 during operation.

According to the present invention, the position of the displacement sensor 8 must be as close as possible at the beveled tip 6 so that the shaft end 4 is as short as possible. The shaft end 4 is the section of the needle 1 which is sensitive to the movements. The shorter the shaft end 4 is the better doctors can locate smaller liquid or gas cavities, while the sensor remains insensitive to forces applied along the shaft due to friction and lateral resistance forces from tissues.

FIGS. 3a and 3b show two outer views of two different preferred embodiments of the first end 5a of the inventive needle 1. FIG. 3c shows a longitudinal cross sectional view of the needle 1 of a further preferred embodiment, FIGS. 3d and 3e two alternatives to it. They all show inventive embodiments built with optical displacement sensors 8. The shaft end 4 of all embodiments comprises a beveled tip 6 with a pointed end 7. Between the shaft 3 and the shaft end 4 is the flexible joint 11 comprising the first notch 12. In all FIG. 2, the first portion 9a of the optical fiber 9 is mounted inside a groove 13 along the shaft 3 close to its outer surface area 2. In the FIG. 3a-e, the first fiber ends 10 can be seen within the first notch 12 close to the outer surface area 2 of the shaft 3. FIG. 4 shows a cross section of the shaft 3 with the groove 13 and the first portion 9a of the optical fiber 9 in the groove 13 close to the outer surface area 2 of the shaft 3. In this embodiment, the needle 1 is a hollow needle 21 suitable for injections with an inner lumen 20 surrounded by a shaft wall 29. The first portion 9a of the optical fiber 9 is attached in the groove 13 within the shaft wall 29 distant from the lumen 20.

It is an advantage to have the displacement sensor 8 directly integrated in the side wall 29 of the shaft 3 distant from the inner lumen 20, because therefore the shape and the function of the needle 1 is the same as the shape of any standard commercial needle. In such an embodiment with an inner lumen 20, the shaft 3 is preferably covered internally at least partially with a mold injected micro insert made of flexible material.

In the FIG. 3a-e, the first fiber end 10 faces a flat reflective surface 14 fixed to the shaft end 4 forming a parallel gap 15 between the first fiber end 10 and the reflective surface 14. Preferably, this reflective surface 14 is a fiber end 14 of a second portion 9b of the optical fiber 9 positioned in the shaft end 4 and aligned with the first portion 9a of the optical fiber 9.

The second portion 9b of the optical fiber 9 is mounted equally as the first portion 9a of the optical fiber 9. It is also mounted inside a groove 17 but along the shaft end 4 close to its outer surface area 2, as shown in FIG. 3c-e. FIG. 4 may also apply to a cross section of the shaft end 4, the optical fiber shown being the second portion 9b of the optical fiber 9 mounted in the groove 17 close to the outer surface area 2 of the shaft end 4. In case of a hollow needle 21, the second portion 9b of the optical fiber 9 is attached in the groove 17 within the shaft wall 29 distant from the lumen 20.

Preferably, the optical fiber 9 is mounted inside a groove 13 and fixed by medical grade epoxy or UV curable adhesive.

According to FIG. 3b, the shaft 3 comprises a second notch 19, also being transverse to the axis A, positioned opposite the first notch 12 in the shaft 3 and in an axial distance T to the first notch 12 leaving a solid portion of the needle 1 between said notches 12, 19. This second notch 19 further softens the flexible joint 11. Preferably, both notches 12, 19 are deep cuts, preferably reaching or passing the axis A.

FIG. 3c shows again a shaft 3 with one first notch 12, wherein this first notch 12 splits at its inner end to both directions of the axis A to a total length L forming a reverse T-like shape 18. The length L is preferably longer than the depth H of the first notch 12. This is an alternative embodiment with a softer flexible joint 11.

FIG. 3d shows a further alternative embodiment of a shaft 3 with one first notch 12, wherein this first notch 12 extends at its inner end towards the direction of the pointed end, in directions of the axis A to a total length L' forming a L-like shape 18'. This has the advantage that the flexible joint 11 moves closer to the area of the beveled tip 6 and the length sensitive to the forces F becomes shorter.

FIG. 3e shows a further alternative embodiment of a shaft 3 with one first notch 12, wherein this first notch 12 begins on the radial orientation where the pointed end 7 is directed to. It extends at its inner end in the direction away from the pointed end, in directions of the axis A to a total length L' forming a L-like shape 18'. Since this notch can be placed very close to the pointed end 7, the shaft end 4 becomes very short, because the flexible joint 11 moves even closer to the area of the beveled tip 6 and the length sensitive to the forces F becomes even shorter.

In all configurations of the first notch 12 having a T-like shape 18 or an L-like shape 18', the end section of the reverse "T" or "L" is preferably bent backwards in direction of the beginning of the notch to reduce the material thickness and to soften the flexible joint 11 thereby.

In a second inventive embodiment of the invention, not shown, the displacement sensor 8 comprises two wires with an electric strain gauge under tension, whereas the notch 12 is bridged by the electric strain gauge under tension connected to said wires. The strain gauge is fixed at the shaft end 4 as well as at the shaft 3 opposite the notch. It may be fixed to a flexible carrier for mounting. In this configuration, the optical fiber 9 of the first embodiment is replaced by wires, and the gap 15 is replaced by the electric strain gauge under tension.

In this second inventive embodiment, the wires are the signal conductor 24 leasing the signals from the electric strain gauge to an evaluation device. All said features characterizing the invention apply accordingly to the second inventive embodiment with the wires and the electric strain gauge instead of the optical fiber 9 and its gap 15.

It is obvious that the displacement sensor 8 must be surrounded by a hermetic sealing. In all of the embodiments described before, the flexible joint 11 is preferably filled with medical grade flexible adhesive. Also preferable is that the shaft 3 and the shaft end 4 are covered externally at least partially with a thin thermo retractable flexible tube.

All embodiments of different needles 1 described before allow high volume cost effective production because they are simple in construction. The needles 1 described are disposable.

The displacement information gained by the displacement sensor 8 is led by a signal conductor 24 for further evaluation. This signal conductor 24 includes the continuation of the first portion 9a of the optical fiber 9 until its second end.

The first portion 9a of the optical fiber 9 or the wires pass the needle hub 22 and the cable 23 attached to the needle hub 22, ending in the said connector 25, as shown in FIG. 1.

Such an inventive needle device is disposable, and it also allows high volume cost effective production.

Alternatively, the second end of the first portion 9a of the optical fiber 9 or the wires may end at an evaluation unit 27 without passing a connector 25. In this case, the evaluation unit 27 is attached to the needle hub 22. In this preferred embodiment of a needle assembly 26 not shown, the evaluation unit 27 of FIG. 6 is attached directly to the syringe 28, with or without a connector 25. This configuration comprises a very small evaluation unit 27, powered preferably by a battery. It can be attached around the syringe 28, being a small and compact unit, flexible in use. Again, the signal conductor 24 contains the first optical fiber 9 or the wires. This needle assembly 26 is also disposable. Since sterilization becomes more and more an issue, medical instruments are the longer the more required to be disposable.

FIG. 6 shows an inventive displacement sensing needle assembly 26 comprising an inventive needle 1, an evaluation unit 27 to which it is attached, and a syringe 28, attached to the needle hub 22. The configuration shown in FIG. 6 is ready for use.

During use of an embodiment with an optical sensor as displacement sensor 8, the elastic deformation of the flexible joint 11 from forces F exerted at the shaft end 4 provides a change in the length of the gap 15, which gap 15 forms the so called optical Fabry-Perot cavity. The evaluation unit receives the output of the first optical fiber 9 and computes a signal dependent on the displacement of the shaft end 4.

In a preferred embodiment a visual or acoustic force feedback signal is generated for giving practitioners direct and continuous information during injection procedures to position the needle in the predetermined anatomical target to be explored and treated. When the needle penetrates solid or semi-solid tissues or organs, axial and radial forces are exerted at the tip, when moving the needle hub 22, whereas in liquid or gaseous environments, no forces are exerted. Thus when the beveled tip 6 is surrounded by liquid or gas, practitioners can apply small movements to the needle to confirm the correct position when no feedback signal is detected. In this position, it is safe to inject the liquid from the syringe 28 through the hollow needle 1 to the body.

Example of a Preferred Embodiment

The displacement sensor 8 is based on Fabry-Perot white light interferometry or on intensity modulation technique using an optical fiber 9 and a moving back reflective surface 14. In a preferred embodiment, the displacement sensor 8 is at its gap 15 not more than the length of the diameter D of the shaft 3 distant from the beveled tip 6, to keep the shaft end 4 small. In an even preferred embodiment, the gap 15 is opposite the beveled tip 6. The shaft diameter D should be of normal size, typically 1 mm, but not larger than 3 mm. The notch 12 is not necessary deeper than half the diameter D. It is usually between ⅓ and ⅔ of the diameter D of the shaft 3.

In case of a hollow needle, the thickness of the shaft wall 29 is typically 0.2 mm, but no larger than 0.4 mm. The gap 15 or Fabry Perot cavity between the fiber end 10 and the reflective surface 14 is between 10 and 30 μm for white light interferometry measurement, and between 10 and 100 μm for light intensity modulation measurement dependent on the type and number of fibers used. The widths W, W' of the notches 12, 19 are between 50 and 300 μm.

The maximum deformation of the first notch 12 near the outer surface area 2 and therefore of the gap 15 due to the applied forces F of up to 2 N is between 1 and 10 μm depending on the design of the parameters L, H and T.

All notches 12, 19 are best made by turning, laser machining or EDM.

LIST OF REFERENCE SYMBOLS 1 needle or hollow needle for invasive medical use
2 outer surface area
3 needle shaft, shaft
4 shaft end
5a first end of the shaft
5b second end of the shaft
6 beveled tip
7 pointed end
8 displacement sensor
9 optical fiber
9a first portion of optical fiber
9b second portion of optical fiber
10 fiber end of first portion of optical fiber
11 flexible joint
12 first notch
13 groove
14 reflective surface, fiber end of second portion of optical fiber
15 gap
18 T-like shape
18' L-like shape
19 second notch
20 lumen
21 hollow needle
22 needle hub
23 cable
24 signal conductor
25 connector
26 needle assembly
27 evaluation unit
28 syringe
29 shaft wall
A axis
D diameter of the shaft
L, L' length
F Force
H, H' height
T distance
W width

The invention claimed is:

1. A needle for invasive medical use, comprising:
a needle shaft defining a longitudinal axis and having an outermost surface area, a tissue piercing pointed end, a lumen, and an opposed hub end;
a flexible joint with a notch extending through the outermost surface area of the shaft proximate the pointed end, wherein the notch is in fluid communication with the lumen;
a displacement sensor associated with the notch for detecting and signaling a displacement of the shaft end relative to a remainder of the shaft resulted from a force applied to the shaft pointed end when the pointed end is moved into contact with body tissue; and
a signal conductor to transmit detected signals from the displacement sensor.

2. The needle according to claim 1, wherein the displacement sensor comprises an optical fiber with a first portion positioned inside the shaft, with a fiber end positioned inside the notch facing a reflective surface fixed to the shaft end and forming a parallel gap between the fiber end and the reflective surface, and wherein the signal conductor contains the optical fiber.

3. The needle according to claim 2, wherein the reflective surface is a fiber end of a second portion of the optical fiber positioned in the shaft end and aligned with the first portion of the optical fiber.

4. The needle according to claim 2, wherein the optical fiber is the sole optical fiber within the needle shaft.

5. The needle according to claim 1, wherein the displacement sensor comprises a miniature electric strain gauge at the flexible joint, connected with a pair of wires, wherein the signal conductor contains the wires.

6. The needle according to claim 1, wherein the needle is a hollow injection needle with the lumen surrounded by a shaft wall, and wherein the signal conductor is within the shaft wall distant from the lumen.

7. The needle according to claim 6, wherein the shaft is internally at least partially covered with a mold injected micro insert made of flexible material.

8. The needle according to claim 1, wherein the notch is transverse to the axis, at least at its outer starting position.

9. The needle according to claim 8, wherein the notch continues at its inner end to one or both directions of the axis to a total length forming a L-like or T-like shape.

10. The needle according to claim 8, comprising a second notch, wherein the two notches are positioned opposite each other and distant from each other in the shaft.

11. The needle according to claim 1, wherein the signal conductor is mounted inside a groove along the shaft open to the outermost surface area.

12. The needle according to claim 1, wherein the notch is filled with medical grade flexible adhesive.

13. The needle according to claim 1, wherein the shaft is covered externally at least partially with heat shrink tubing.

14. The needle according to claim 1, wherein the signal conductor is fixed by medical grade epoxy or UV curable adhesive.

15. The needle according to claim 1, wherein the signal conductor passes the needle hub ending in a connector or in an evaluation unit at the second end.

16. A needle assembly comprising the needle according to claim 15, a syringe attached to said needle hub and an evaluation unit connected to said signal conductor.

17. The needle assembly according to claim 16, wherein the evaluation unit is attached to the syringe.

18. The needle assembly according to claim 16, wherein the needle assembly is disposable.

19. An injection needle for invasive medical use, comprising:
a needle shaft having a distal end forming a tissue piercing beveled end and a proximate end having a hub;
a flexible joint with a notch forming a gap within the needle shaft, the gap positioned a distance away from the beveled tip not more than the diameter of the shaft;
a displacement sensor associated with the notch for detecting and signaling a displacement of the beveled end relative to the rest of the shaft resulting from a force applied to the beveled end when the beveled end is moved into contact with body tissue; and
a signal conductor to transmit detected signals from the displacement sensor.

20. An injection needle for invasive medical use, comprising:
a needle shaft having a hollow body with opposed distal and proximal ends and a lumen, the distal end forming a tissue piercing beveled end, and the proximate end having a hub;
a notch extending through an outermost exterior surface of the body towards a central axis of the body, the notch in fluid communication with the lumen, the notch positioned adjacent the beveled end whereby the beveled end is displaceable relative to a remainder of the body by flexible bending of the body at the notch when the beveled end is pressed against body tissue;
a displacement sensor associated with the notch to detect and signal a displacement of the beveled end relative to the remainder of the body; and
a signal conductor extending away from the notch to transmit detected signals from the displacement sensor exterior to the body when the beveled end is pressed against body tissue inside the body.

* * * * *